United States Patent
Baker et al.

(10) Patent No.: US 6,562,332 B2
(45) Date of Patent: May 13, 2003

(54) ATTRACTANTS OF BENEFICIAL INSECTS

(75) Inventors: Thomas C. Baker, Ames, IA (US); John J. Obrycki, Ames, IA (US); Junwei Zhu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/730,486

(22) Filed: Dec. 5, 2000

(65) Prior Publication Data

US 2001/0043937 A1 Nov. 22, 2001

Related U.S. Application Data

(63) Continuation of application No. PCT/US00/10795, filed on Apr. 21, 2000.
(60) Provisional application No. 60/130,334, filed on Apr. 21, 1999.

(51) Int. Cl.[7] .................. A01N 31/04; A01N 31/08; A01N 37/10; A01N 35/04; A01N 35/06
(52) U.S. Cl. ................ 424/84; 424/409; 514/532; 514/546; 514/678; 514/688; 514/699; 514/729; 514/730; 514/731; 514/964
(58) Field of Search .............. 424/84, 409; 514/730, 514/532, 546, 678, 688, 699, 729, 731, 964

(56) References Cited

U.S. PATENT DOCUMENTS 5,308,613 A   5/1994   Banfield ................ 424/84

OTHER PUBLICATIONS

Chemical Abstracts 131:127829, 1999.*
Dicke, M., et al., "Isolation and Identification of Volatile Kairomone that affects acarine Predator–Prey Interactions: involvement of host plant in its production", *J. Chem. Ecol.*, vol. 16, No. 2, Accession No. 1990:232528, 381–396, (1990).
Hedine, P.A., et al., "Identification of some volatile constituents of the Lady Beetle *Coleomegilla maculata* lengi (Timberlake): search for pheromones", *J of the Mississippi Academy of Sciences*, vol. 44, Accession No. 90:67108, 59–66, (1988).
Ter–Simonyan, L.G., et al., "Integrated protection of cabbage", *Zashch. Rast.*, vol. 5, (Russia), Accession No. 1982:402238, 48–49, (1982).
Ushchekov, A.T., "Attraction of Aphid Enemies to Greenhouses", *Zashchita Rastenii*, No. 8, (Russia), Accession No. 78:26370, 32, (1977).

* cited by examiner

*Primary Examiner*—John Pak
(74) *Attorney, Agent, or Firm*—Schwegman, Lundberg, Woessner & Kluth, P.A.

(57) ABSTRACT

The invention provides methods and compositions useful for attracting predatory insects.

8 Claims, 13 Drawing Sheets

ATTRACTANTS OF BENEFICIAL INSECTS

CROSS-REFERENCE TO RELATED APPLICATIONS

This application is a continuation of International Patent Application No. PCT/US00/10795, filed Apr. 21, 2000, which application was published in English under PCT Article 21(2), which claims priority to U.S. Provisional Application No. 60/130,334, filed Apr. 21, 1999.

BACKGROUND OF THE INVENTION

The use of predatory insects, including coccinellids and chrysopids, as biological control agents to suppress pest populations on either economically important crops or in home gardens, is widely accepted and recognized by the general public and biological control practitioners (see references in, Obrycki, J. J. and Kring, T. J., 1998, *Annu. Rev. Entomol.* 43:295–321; and Canard, M., et al., 1984. Biology of Chrysopidae, pp. 294, DR W. JUNK Publishers, The Hague/Boston/Lancaster).

There have been significant successes in using coccinellids and chrysopids to suppress whitefly, aphid, mealybug, scale and mite populations (Gerling, D. 1990). Natural enemies of white flies: predators and parasitoids. In Whiteflies: Their Bionomics, Pest Status and Management. (D. Gerling, ed.), pp. 147–185. Andover: Intercept Ltd.; and in Frazier, B. D. 1988, Coccinellidae. in Aphids-Their Biology, Natural Enemies and Control. (A. K. Minks, P. Harrewijn, eds.), Vol. B, pp. 231–247. New York, Amsterdam: Elsevier; New, 1975).

Despite the significant use of these two groups of predatory insects for biological control, very little is known about the mechanisms involved in prey location (e.g. van Emden, H. F., and Hagen, K. S., 1976, *Environ. Entomol.* 5:469473; and HAGEN, K. S. 1987. Nutritional ecology of terrestrial insect predators. In Nutritional Ecology of Insects, Mites, Spiders, and Related Invertebrates, (Slansky and Rodriguez, eds.), pp. 533–577. New York: Wiley and Sons.). In particular, it is not known whether the predators are able to use odors directly from their prey or their host plant to eventually locate their prey. Because of the dispersal behavior of many aphidophagous species and their polyphagous nature (Frazier, 1988), attractive compounds could be useful in retaining predaceous insects in fields where they were released.

The twelve spotted lady beetle, *Coleomegilla maculata* (Degeer) and the golden eyed green lacewing, *Chrysoperla carnea* (Stephens) are two of the most common aphid predators found in field crops in the eastern United States. They are especially abundant in crops such as cotton, corn and alfalfa. In corn these two predatory species feed on aphids and European corn borers (Obrycki and Kring, 1998; Phoofolo, M. W, 1997, pp. 172, Ph.D. thesis, Iowa State University; Sparks, A. N., et al., 1966, *J. Econ. Entomol.* 59:104–107; and Udayagiri, S., 1996, *Agric. Zool. Rev.* 7:181–216), and in alfalfa they feed on aphids and alfalfa weevil larvae (Giles, K. L., et al., 1994, *Biol. Cont.* 4:170–177).

In spite of the successes that have been reported using predatory insects to control pests, there is currently a need for methods to attract predatory insects to target areas. There is also a continuing need for additional forms of pest control that do not require the use of hazardous or toxic chemicals.

SUMMARY OF THE INVENTION

Applicant has discovered that certain plant volatiles emitted for instance from corn, alfalfa, and from plant parts such as flowers and fruits of various species are useful for attracting predatory insects. Accordingly, the invention provides a method for attracting a predatory insect to a target area comprising applying an effective amount of a plant volatile in or near the area. Preferably, the plant volatile is not β-caryophyllene or (E)-β-Farnesene.

The invention also provides a composition comprising an effective insect attracting amount of a plant volatile, and a suitable carrier.

DETAILED DESCRIPTION

Figure 1:
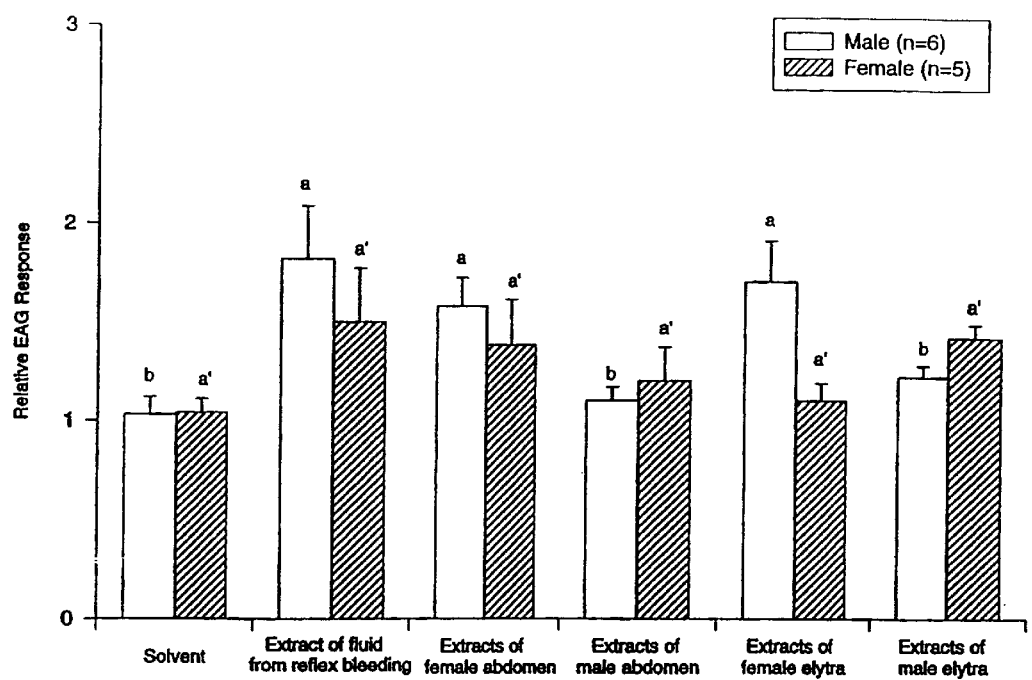
FIG. 1. Shows EAG responses of male and female *Coleomegilla maculata* to various extracts from conspecific body parts and the fluid of reflex bleeding. Means (±standard error) with different letters are significantly different (ANOVA followed by FPLSD test, $P < 0.01$).

As used herein, the term 'predatory insect' includes members of the family Coccinellidae (lady beetles) and Chrysopidae (green lacewings). For example, the term includes insects of the species, *Coleomegilla maculata*, and of the species *Chrysoperla carnea*.

The compounds useful in the methods of the present invention include volatile compounds found in host plants (e.g. host plants of the predatory insect's prey), as well as in fruits and flowers that would provide nutrition to the adult predators. Preferred plant volatiles useful in the methods of the invention include monoterpene alcohols, and phenolics, such as phenyl alcohols, phenyl esters, phenyl aldehydes and phenyl ketones. For example, see, Hammack, L., 1997, Environmental Entomology Vol. 26, No. 2. p311–317; Flath, R. A., et al., 1978, Journal of Agricultural Food and chemistry Vol, 26, No. 6, 1290–1293; and Hibbard, B. E., et al., 1997, *Enviornmental Entomology,* 26, 285–295. Preferred compounds are 2-Phenylethanol, phenylacetaldehyde, and α-Terpineol.

Applicant has discovered that volatile plant compounds can be used to attract adult predatory insects that prey on unwanted pests. The compositions and methods of the invention can be used to attract adult predatory insects to any area where their presence may be desired. The adult females and males are attracted and can themselves consume the prey. In addition, the females that are attracted to the area can lay eggs on the plants near prey, with the larval offspring then consuming the prey.

As used herein, the term 'attract' includes both drawing predatory insects to an area, as well as retaining predatory insects in an area once they are there (e.g. due to reiterative drawing effects).

As used herein, the term 'applying' includes any suitable method of emitting an effective attractive amount of a plant volatile compound in an area. For example, the term includes the broadcast or restricted localized spraying of a volatile in or around an area, with or without first microencapsulating the volatile, emitting the volatile from one or more controlled-release point-source dispensers placed in or around an area, and integrating the release of the volatile with an irrigation technique ('chemigation').

As used herein, the term 'controlled-release point-source dispenser' includes any suitable method for controlling the emission rate of the volatile compound from a concentrated source reservoir of the compounds. Such methods include, but are not limited to: pads, beads, rods, spirals, or balls comprised of rubber, leather, cotton, wood or wood products, polyethylene, polypropylene or polyvinyl chloride that are impregnated with the volatile compound; microcapillary tubes open at one end; sealed polyethylene or polypropylene tubes sealed at both ends; laminates comprised of layers of the volatile compound alternated with plastic and cut in various sized flakes or preserved as large ribbons or sheets; permeable or semi-permeable membranes covering a non-permeable container serving as a reservoir for the volatile compounds; large porous beads or sponges; micro-capsules; sealed envelopes or bags made of polyethylene, polypropylene, paper, or other permeable substances, metered aerosol systems utilizing pump or pressure technologies to emit aerosolized droplets of the volatiles into the atmosphere, onto plants surfaces or dirt, or onto any of the above controlled-release point-source dispensers; and non-aerosol micro-pump technologies that cause metered quantities of the compounds to be dispensed and volatilized by any of the above methods.

As used herein, the term "target area" includes any place where the presence of predatory insects may be desirable, such as, for example, a farm field, a garden, or a horticultural or floricultural nursery.

Useful amounts to evoke attraction (attractive amounts) will depend on the application technique employed and on the specific conditions of the area at the time of application. Such amounts can readily be determined by one skilled in the art. From controlled-release point-source dispensers the reservoir amounts will typically be about 50 µg or higher and release rates will be about 10 ng/min or higher. Release rates from 1 $cm^2$ of surface to which chemigation or microencapsulated or neat volatiles are applied will typically be about 10 ng/min or higher.

The invention will now be illustrated by the following non-limiting Example.

EXAMPLE 1

Materials and Methods

Insects.

*Coleomegilla maculata* adults were collected from an overwintering site in Roland, Iowa. Larvae of *C. carnea* were purchased from Rincon-Vitova, California, and reared at 20° C., 16:8, light-dark period. Females were mated and produced eggs. Larvae were fed with pea aphids, *A. pisum* and frozen *Ephestia kuehniella* eggs until pupation. Adults were sexed and kept in separate cages until used in experiments.

Extraction of Potential Sex Pheromone-like Substances from *C. maculata*.

Adults of both sexes were anesthetized by placing them at −20° C., then the abdomen and elytra of adults were cut off with a pair of fine scissors. Dissecting tools were rinsed with acetone several times between dissections to avoid cross-contamination. The dissected parts were extracted in a 1-ml vial containing 500 µl of hexane for two hours. Ten males and females were dissected and extracted. The extracts were concentrated to 200 µl under a mild stream of $N_2$. Approximately 20 µl of the extracts, equivalent to one adult, was used for the EAG tests.

Collection of Defensive Compound Extracts.

Both sexes of C. maculata were handled vigorously, and pressed against a piece of filter paper (Whatman, No. 1), resulting in reflex bleeding production of orange colored fluid excreted through the joints of the legs, that was absorbed into the filter paper. Fluids from 20 beetles were collected. The filter paper used for the collection was then cut into small pieces and placed in a 2-ml vial and extracted with 200 µl of hexane for one hour. A volume of 10 µl of the concentrated extract was used for EAG tests.

Collection of Plant Volatiles.

Corn (Pioneer, Hybrid 3489) was grown in the greenhouse under approx. 25° C. and 75% humidity, with natural light supplemented by 400 Watt high pressure sodium lights. The three-leaf stage of plants was used for volatile collections, because this life stage is infested by corn leaf aphids (Bing, J. W., et al., 1992, J. Econ. Entomol.21:223–234) and it is also a stage searched by these predatory species. Corn leaves were removed from plants, and ca. 15 g placed in a 0.5–1 glass collector with two openings on each side. A stream of purified air passing through a freshly activated charcoal filter was blown into the inlet of the collector, through the corn leaves, then exited through the outlet connected to a Tenax trap. The trap consisted of a Pasteur pipette (5 cm long and 0.5 cm diameter) packed with 300 mg of Tenax (20–35 mesh, Alltech, Ill.). The flow rate of the air was 150 ml/min from the outlet of the Tenax trap, and the volatiles were collected for 18 hours. The trapped volatiles were eluted with HPLC-grade hexane. The extracts from three collections were combined and concentrated to 100 µl. Ten microliters of extracts were used for each EAG test.

Extracts of Catnip.

Dried seeds and flowers of catnip, Nepeta cataria, were purchased from a local pet store. For EAG tests, approx. 0.2 mg of dried plant material was homogenized, then extracted by adding 500 µl of hexane. The extract was poured through a funnel with filter paper (Whatman No.1), and the residue was discarded. The extract was concentrated to 100 µl, under a mild stream of $N_2$. The extract was then stored at −20° C. until used in EAG tests.

Electroantennogram Responses.

EAG recordings were made by connecting an electrogel-filled (Spectro 360, Parker Laboratory, New Jersey) glasspipette Ag/AgCl electrode to the head of an excised beetle or lacewing. A recording electrode filled with the same electrogel connected to a high-impedance DC amplifier with automatic baseline drift compensation, was placed in contact with the tip of their antennae (intact). Antennal responses to various chemical stimuli were first recorded for a series of commercial synthetic compounds representing known corn leaf volatiles. Then, male and female body extracts of C. maculata, reflex bleeding extracts, aphid alarm pheromone and catnip extracts were tested. A second series of EAG tests was then conducted including dose-response series using selected EAG-active compounds from the first test. Serial dilutions of the tested compounds were made in redistilled HPLC-grade hexane at dosages ranging from 0.1 µg to 1000 µg, except α-terpineol, for which methylene chloride was used. The tested compounds and extracts were applied to filter-paper strips (0.5×2.5 cm, Whatman No.1) in 10 µl of solvent, except as otherwise noted. The filter-paper strips were inserted into Pasteur pipettes (15 cm long). Control puffs of air were applied after each puff of a test stimulus. The response to the air puff was used to normalize beetle or lacewing responses relative to the tested stimuli. The average EAG response to the air puff from antennae of C. maculata and C. carnea was 0.05±0.003 mV (n=30) and 0.02±0.001 mV (n=27), respectively. The relative EAG response of each stimulus was normalized by dividing the amplitude of the test stimulus by the mean of the response to the control puff. The sequence of exposure of each stimulus to each antenna was randomly defined.

Chemicals.

Ten corn volatile compounds were used, and the source and purity of these compounds are listed in Table 1. The two aphid sex pheromone components, (4aS,7S,7aR)-nepetalactone and (1R,4aS,7S,7aR)-nepetalactol were kindly provided by Dr. John Pickett of the IACR-Rothamsted, UK. The purity of these two compounds was approx. 97% and 55%, respectively, as analyzed by GC-MS.

TABLE 1

| Compound | Source | Purity (%)* |
|---|---|---|
| (E)-β-Farnesene | Bedoukian Research Inc. | >99 |
| α-Terpineol | Bedoukian Research Inc. | >99 |
| α-Pinene | Aldrich Chemical Co. | 95 |
| (Z)-3-Hexenal | Bedoukian Research Inc. | >99 |
| 2-Phenylethanol | Bedoukian Research Inc. | >99 |
| (E)-2-Hexenal | Sigma Chemical Co. | >99 |
| β-Caryophyllene | K & K Laboratories | >98 |
| 1-Hexanol | Sigma Chemical Co. | 98 |
| (Z)-Hexenol | Bedoukian Research Inc. | >99 |
| 1-Octen-3-ol | Bedoukian Research Inc. | >99 |

Field Test.

A field trapping test was conducted in an alfalfa field in Ames, Iowa. Synthetic compounds at a dose of 50 mg were prepared in hexane or methylene chloride. Medical peerless cotton rolls (5 cm long, 100% cotton) were used as dispensers, and the traps used were similar to the Rebell Trap (Great Lakes IPM, Mich.). The trap was hung from the bent end of an electric farm post, 1.2 m above the ground. Within a replicate (N=3), traps were set at least 10 m apart. The traps were checked daily, and trap position within a series was randomized to minimize the effects of habitat heterogenity.

Statistics.

The resulting EAG data (means of relative responses) and trap catches (means of trapped species) were compared by analysis of variance followed by Fisher's protected least significant difference test (FPLSD).

Results

Selectivity.

In general, the antennae of both sexes of the two predatory species, C. maculata and C. carnea, responded strongly to several green leaf volatiles and sex pheromones of their aphid prey. No obvious differences in the sizes and morphologies of their receptor organs were observed between the two sexes of the same species. Within each species, slight differences in EAGs to each of the tested stimuli were noted, but only two of them were statistically different.

Response to Crude Extracts.

Figure 2:
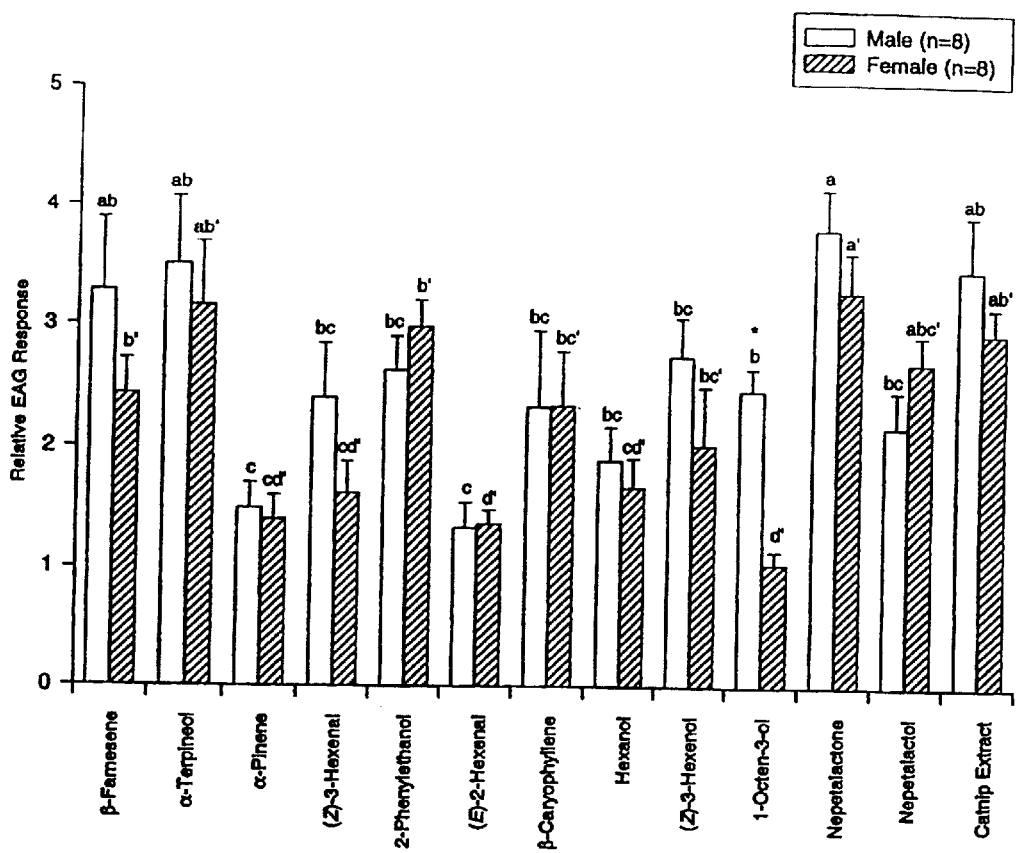
FIG. 2. Shows EAG responses of male and female antennae of *Coleomegilla maculata* to several synthetic corn leaf volatile compounds, sex pheromone components of aphids and a crude extract of catnip. Means (±standard error) with different letters are significantly different (ANOVA followed by FPLSD test, $P < 0.05$). An asterisk above the letter indicates a significant difference in EAGs between male and female antennae in response to this compound (Student T-test, $P < 0.001$).
Figure 3:
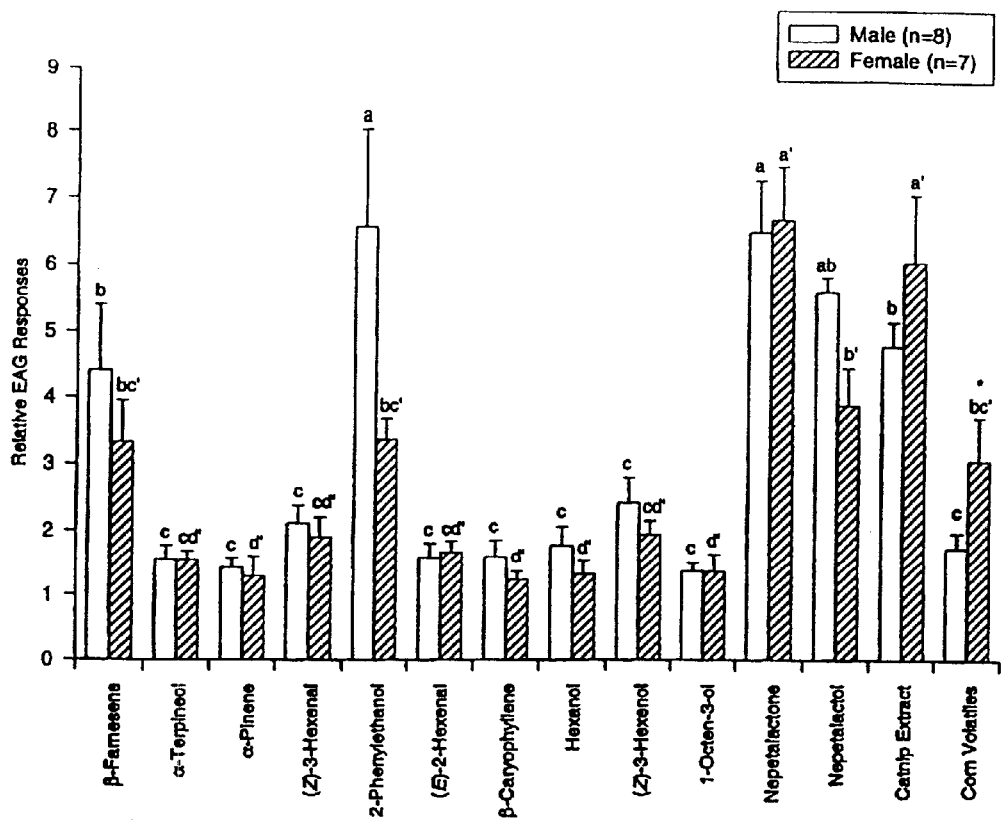
FIG. 3. Shows EAG responses of male and female antennae of *Chrysoperla carnea* to several synthetic corn leaf volatile compounds, sex pheromone components of aphids and the crude extract of catnip. Means (±standard error) with different letters are significantly different (ANOVA followed by FPLSD test, $P < 0.05$). An asterisk above the letter indicates a significant difference in EAGs between male and female antennae in response to this compound (Student T-test, $P < 0.05$).

In C. maculata, female extracts of both the whole abdomen and the elytra elicited higher EAG responses from male antennae, compared with those of male extracts (FIG. 1). The extracts from the defensive "reflex bleeding" also elicited EAG responses. Both male and female antennae responded strongly to catnip extracts (FIG. 2). In C. carnea, no significant EAG responses were observed when stimulated with the extract of C. maculata reflex bleeding (data not shown here), but significant EAG responses were elicited when tested with catnip extracts (FIG. 3). EAG response of female *C. carnea* antenna to extracts of corn leaves was greater than that of males.

Response to Corn Leaf Volatiles.

Ten common corn leaf volatiles, which have been identified from corn leaves (Hammack, L., 1997, Environmental Entomology Vol. 26, No. 2. p311–317; Flath, R. A., et al., 1978, Journal of Agricultural Food and chemistry Vol, 26, No. 6, 1290–1293; and Hibbard, B. E., et al., 1997, *Enviornmental Entomology,* 26, 285–295), were selected for a standard EAG test. In both sexes of *C. maculata*, antennae responded to most of the tested compounds. Responses to (E)-β-farnesene, α-terpineol and 2-phenylethanol were significantly higher than those to α-pinene or (E)-2-hexenol (FIG. 2). However, a significantly higher EAG response was elicited by 1-octen-3-ol from male antenna, relative to that of a female's (FIG. 3). In *C. carnea*, only two corn volatile compounds elicited positive EAG responses, with a significant response from 2-phenylethanol and (E)-β-farnesene, respectively (FIG. 3).

Response to the Sex Pheromone and the Alarm Pheromone of Aphids.

Both sexes of the two investigated species responded to sex pheromone components used by their prey species, (4aS,7S,7aR)-nepetalactone and (1R,4aS,7S,7aR)-nepetalactol. In *C. maculata*, a relatively higher EAG response was elicited by (4aS,7S,7aR)-nepetalactone than that by the alcohol (FIG. 2). Aphid alarm pheromone, (E)-β-farnesene, elicited EAG responses from male antennae as high as those in response to aphid sex pheromone. In *C. carnea*, there were no significant differences between male and female EAGs to aphid sex pheromone components (FIG. 3). However, female antennae of *C. carnea* responded to (4aS,7S,7aR)-nepetalactone greater than to (1R,4aS,7S,7aR)-nepetalactol.

Sensitivity

Figure 4:
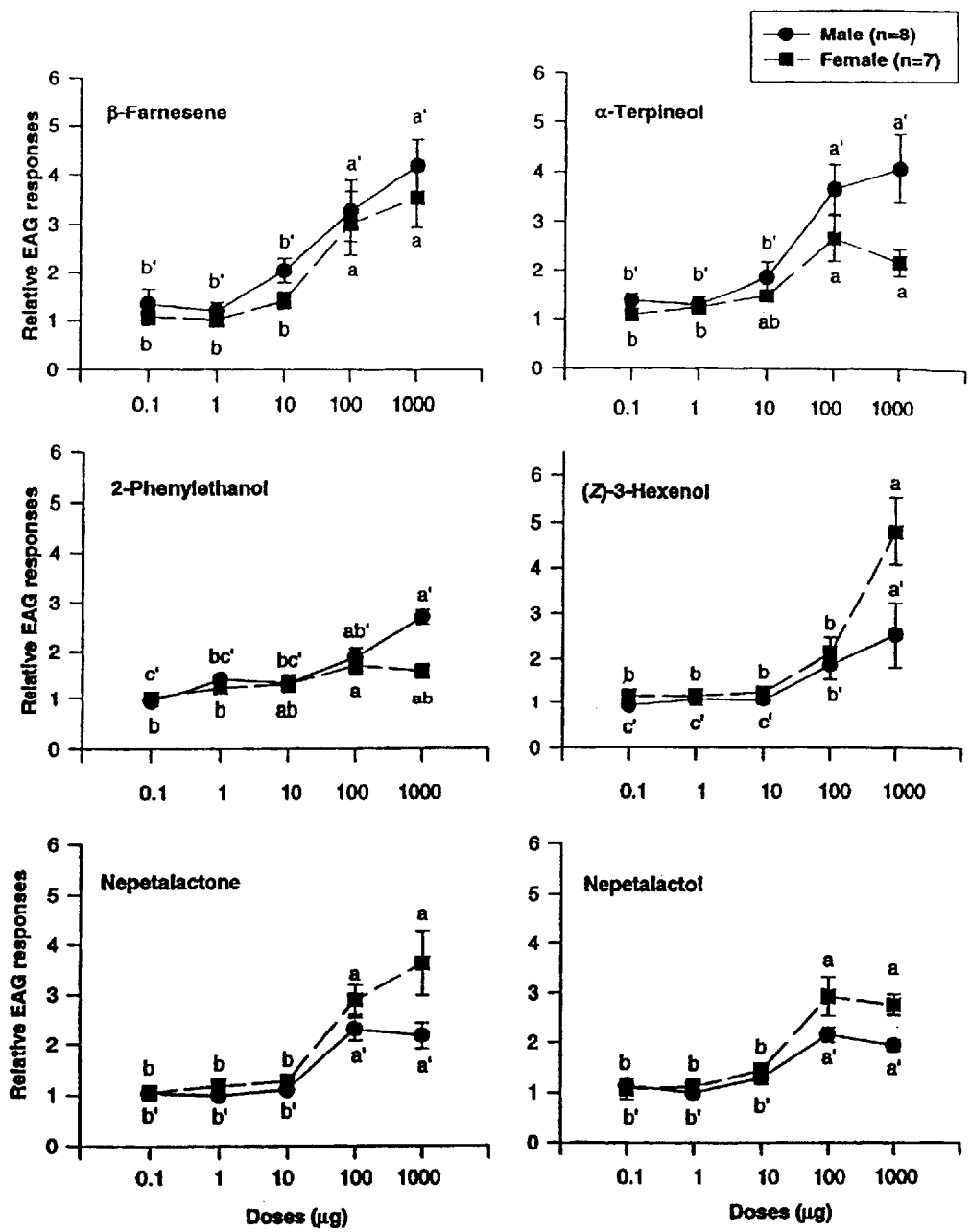
FIG. 4. Shows dose-response curves constructed from EAGs of male and female of *Coleomegilla maculata* to four synthetic corn leaf volatile compounds and two sex pheromone components of aphids. Means of different dosages among different stimuli with the same letter are not significantly different (ANOVA followed by FPLSD test, $P > 0.05$).

EAG responses in *C. maculata* increased with increasing doses of the selected synthetic corn volatile compounds (FIG. 4). EAG dose-response curves showed that male antennae reached saturation at the dose of 100 µg for two of the tested corn volatile compounds, (E)-β-farnesene and α-terpineol (FIG. 4). Female antennae were sensitive to α-terpineol and 2-phenylethanol with significant EAG responses elicited at a dose of 10 g. In response to (4aS,7S,7aR)-nepetalactone and (1R,4aS,7S,7aR)-nepetalactol, the minimum dose for a significant EAG response from both male and female antennae was 100 µg, and saturation likewise occurred at this same dose (FIG. 4).

Figure 5:
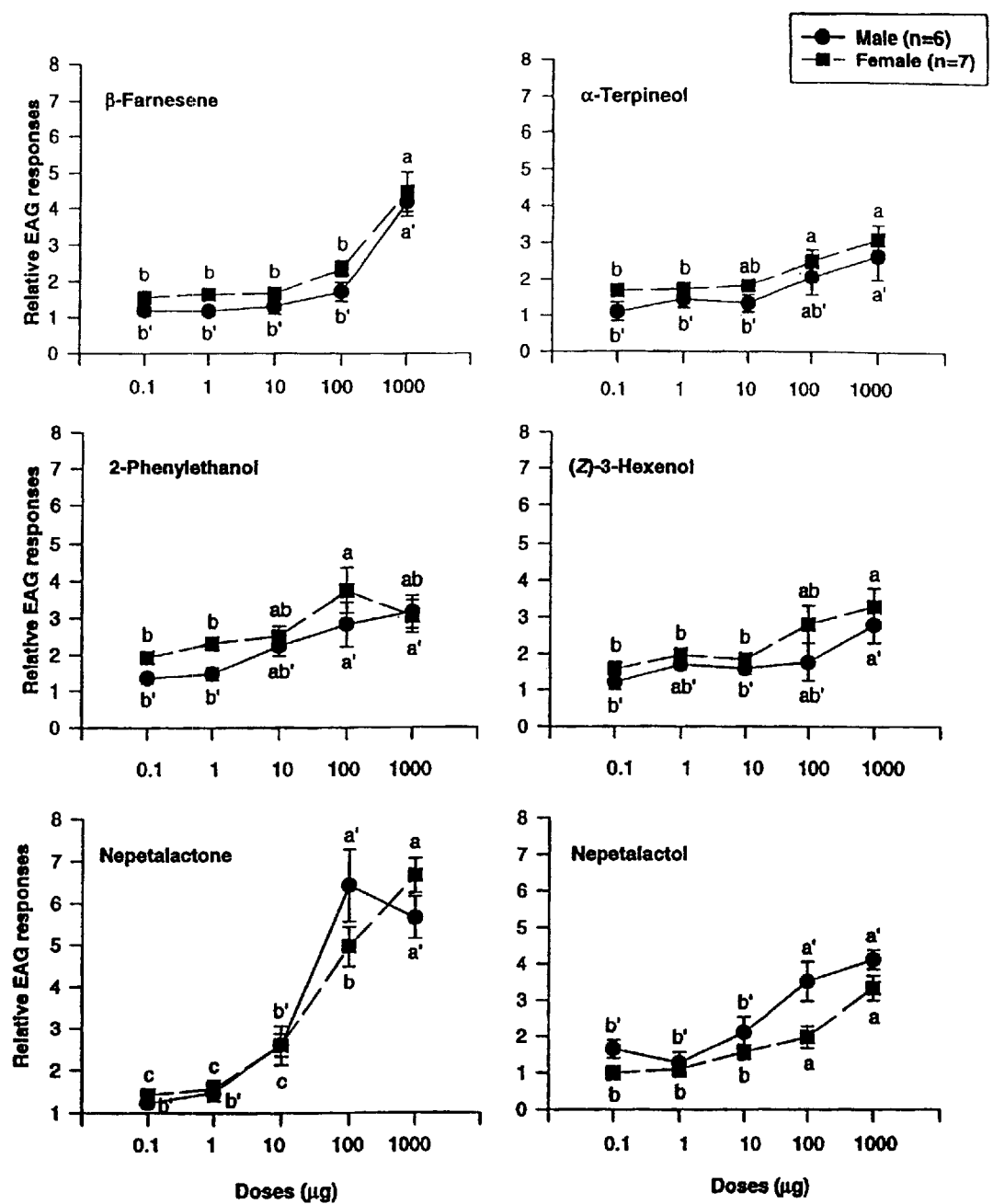
FIG. 5. Shows dose-response curves constructed from EAGs of male and female of *Chrysoperla carnea* to four synthetic corn leaf volatile compounds and two sex pheromone components of aphids. Means of different dosages among different stimuli with the same letter are not significantly different (ANOVA, FPLSD test, $P > 0.05$).

In *C. carnea*, both response curves of male and female antennae in response to the tested corn volatile compounds exhibited significant differences in response sensitivity (FIG. 5). EAG responses of both sexes to (E)-β-farnesene increased with increasing doses, and the highest EAG response was observed at a dose of 1000 µg. Significant EAG responses were elicited from the antennae of both sexes to 2-phenylethanol at 10 µg dosage. No significant differences in EAG responses among the three higher tested doses of this compound were observed. In contrast, the other two corn volatile compounds (α-terpineol and (Z)-3-hexenol) elicited relatively lower EAG responses at all dosages tested. For the two aphid sex pheromone components, the same trends were observed as those shown in *C. maculata*. Saturation appeared at a dose of 100 µg for both compounds in both sexes.

Field Tests

Figure 6:
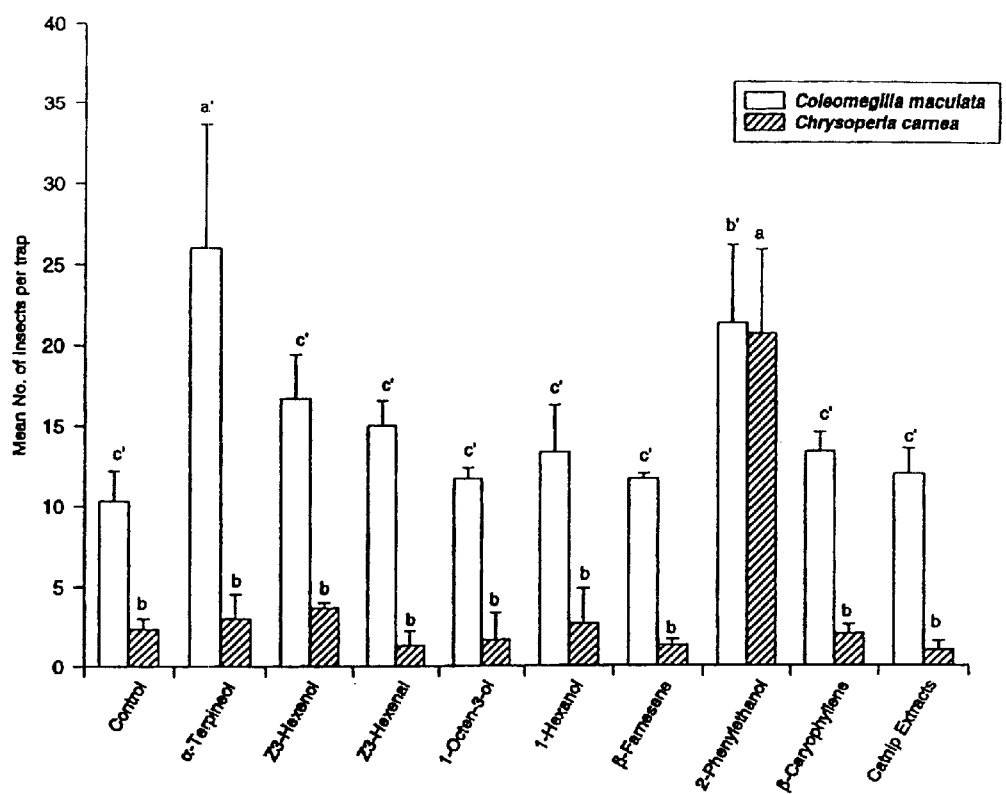
FIG. 6. Shows the mean number of *Coleomegilla maculata* and *Chrysoperla carnea* caught in traps baited with corn volatile compounds (50 mg) and crude extracts of catnip in the alfalfa field (Line indicates S.E.). Columns with the same letter are not significantly different (ANOVA, FPLSD test, $P > 0.05$).
Figure 7:
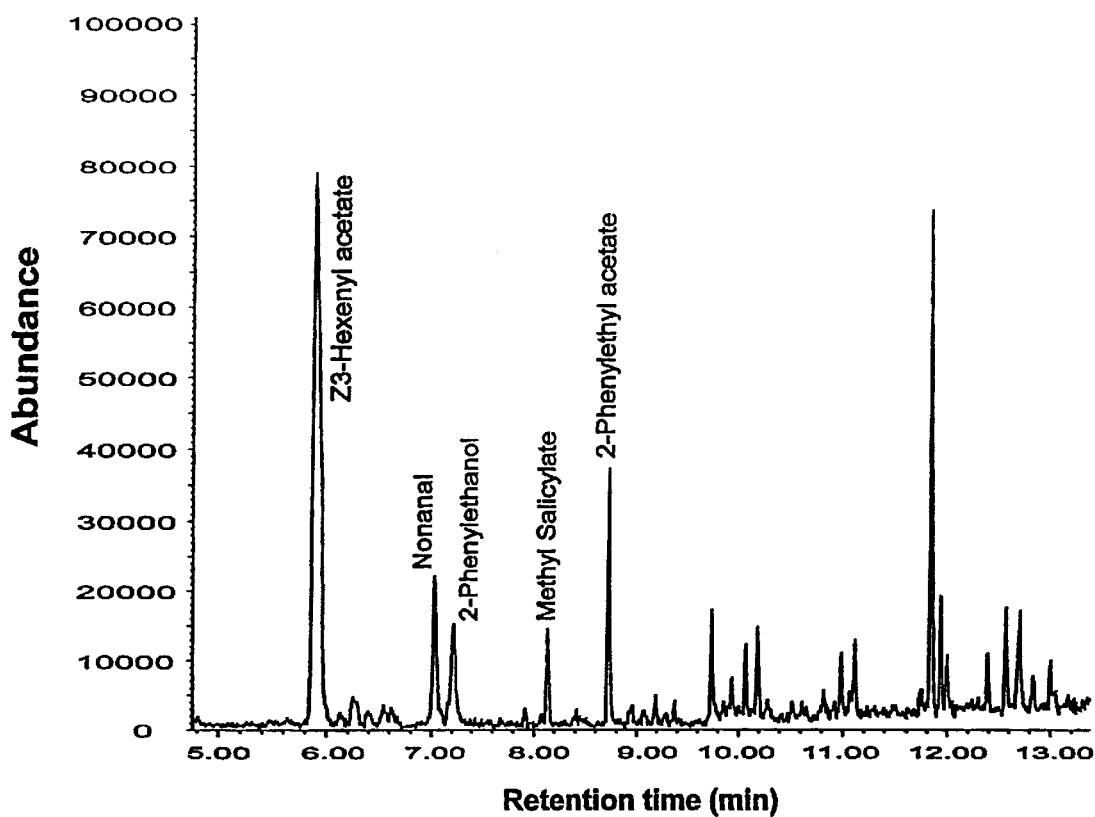
FIG. 7. Shows a capillary gas chromatography ('GC') profile for volatiles collected from the airborne emissions of alfalfa plants. Labeled GC-peaks indicate the volatile constituent was identified using mass spectrometry coupled with GC retention time indices.
Figure 8:
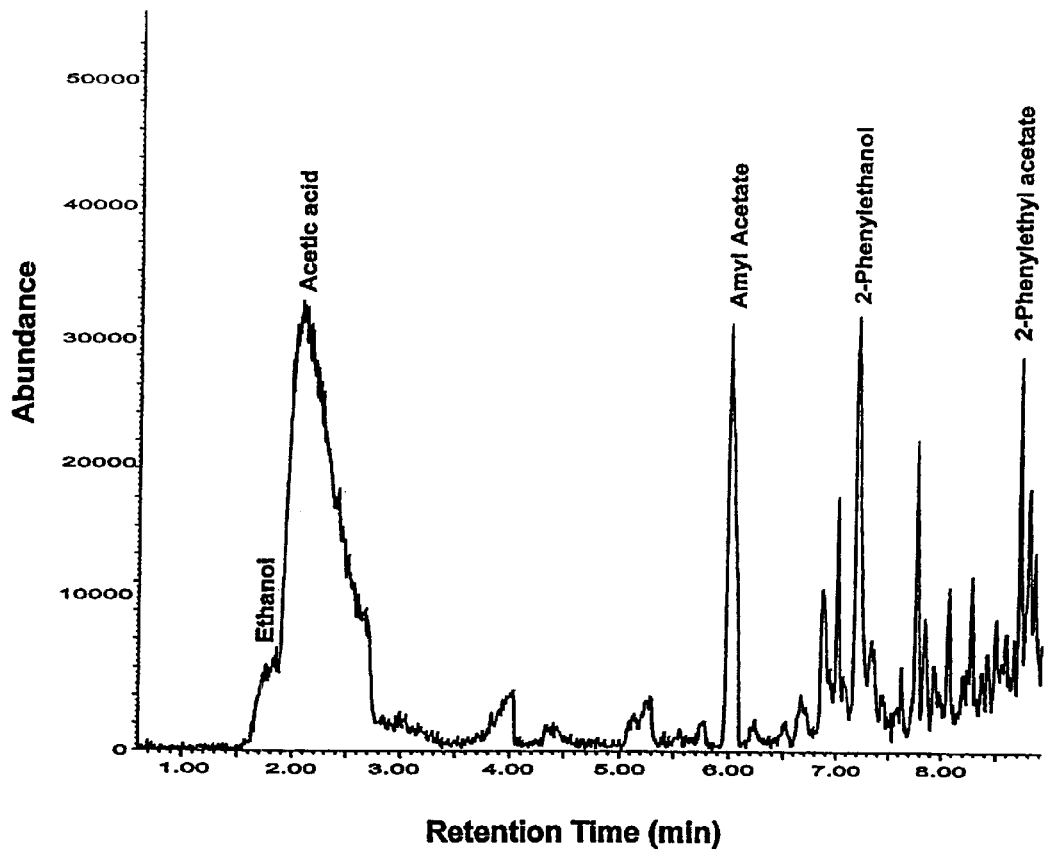
FIG. 8. Shows a capillary gas chromatography ('GC') profile for volatiles collected from the airborne emissions of mango fruits. Labeled GC-peaks indicate the volatile constituent was identified using mass spectrometry coupled with GC retention time indices.
Figure 9:
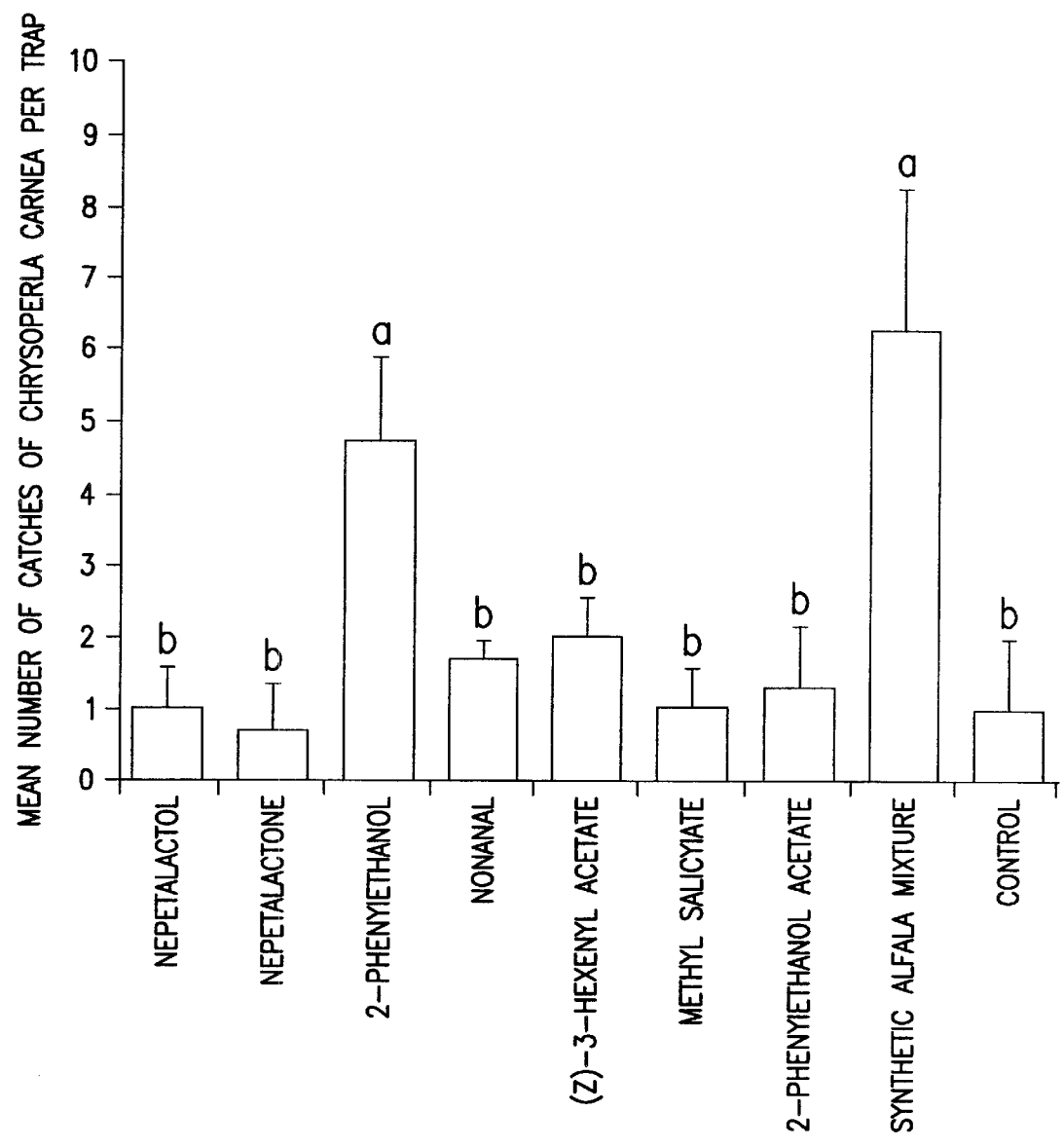
FIG. 9. Shows the mean number of *Chrysoperla carnea* caught in an alfalfa field in traps baited with corn volatile compounds (100 mg on a cotton wick) and a synthetic mixture of identified alfalfa volatiles that includes 2-phenylethanol (see FIG. 1. above). Bars above the means indicate standard errors, and means having no letters in common are significantly different from each other (ANOVA, FPLSD test, P<0.05).
Figure 10:
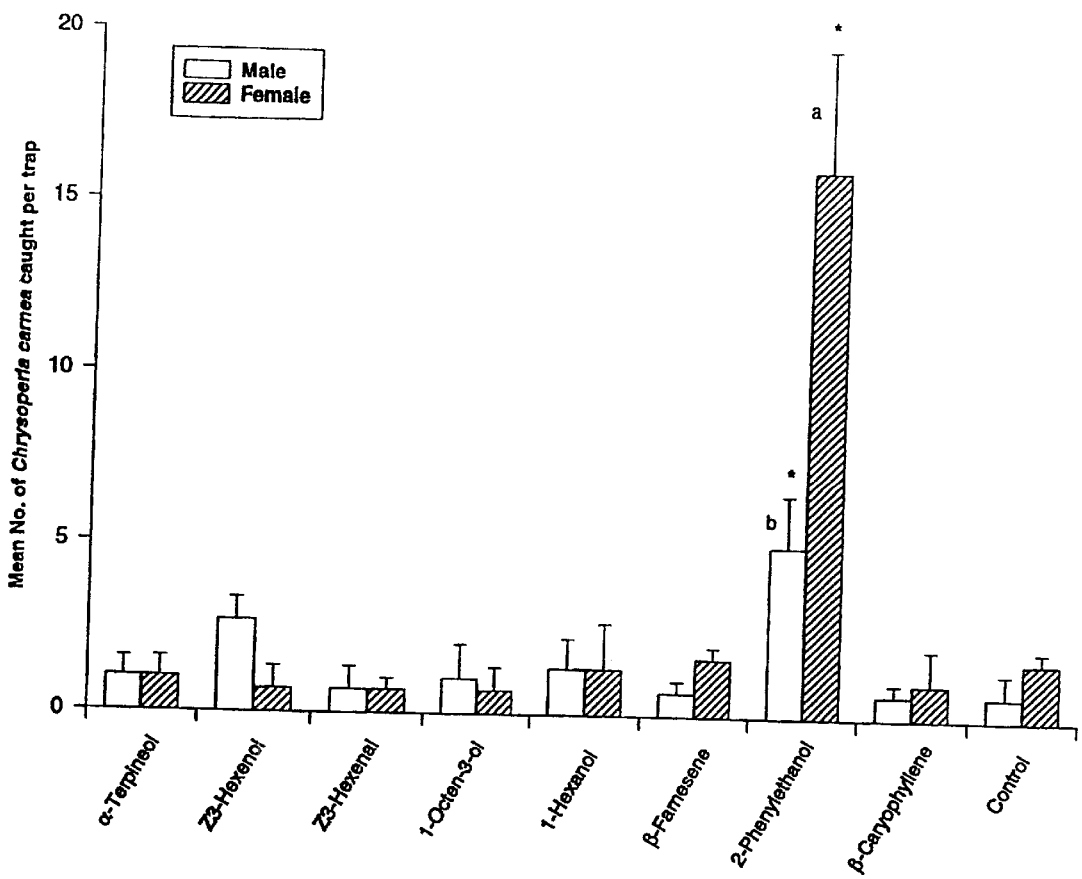
FIG. 10. Shows the mean number of male and female *Chrysoperla carnea* caught along the borders of alfalfa and corn fields in traps baited with corn volatile compounds (100 mg on a cotton wick). Bar above the mean indicates standard error. The asterisks indicate mean captures levels significantly different from those of the rest of the treatments, and the different letters indicate significantly different capture levels between males and females (ANOVA, FPLSD test, P<0.05).
Figure 11:
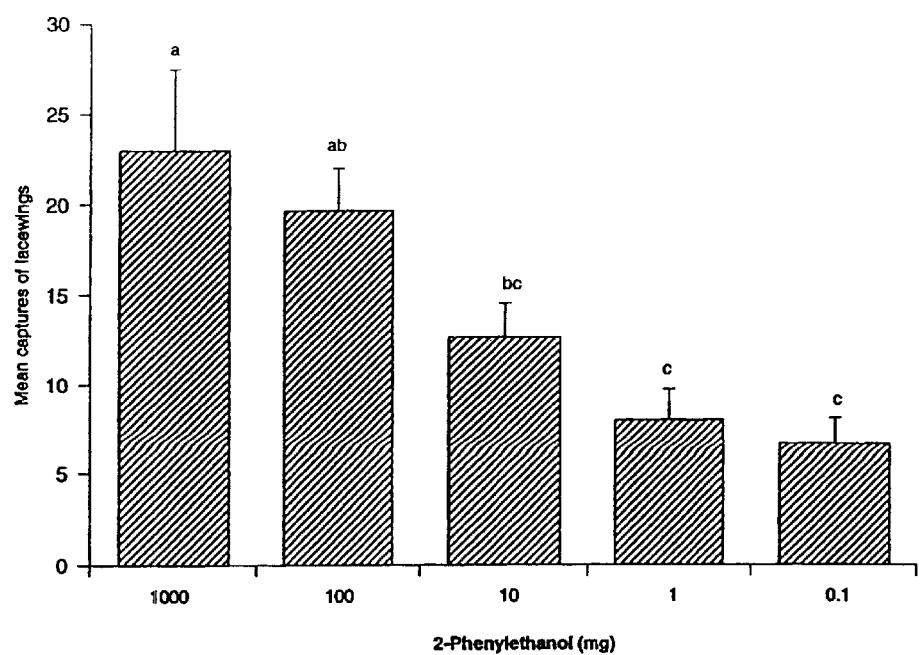
FIG. 11. Shows the relationship between dose of 2-phenyl ethanol on a cotton wick and the capture of *Chrysoperla carnea* adults in an alfalfa field. Bars above the means indicate standard errors, and means having no letters in common are significantly different from each other (ANOVA, FPLSD test, P<0.05).
Figure 12:
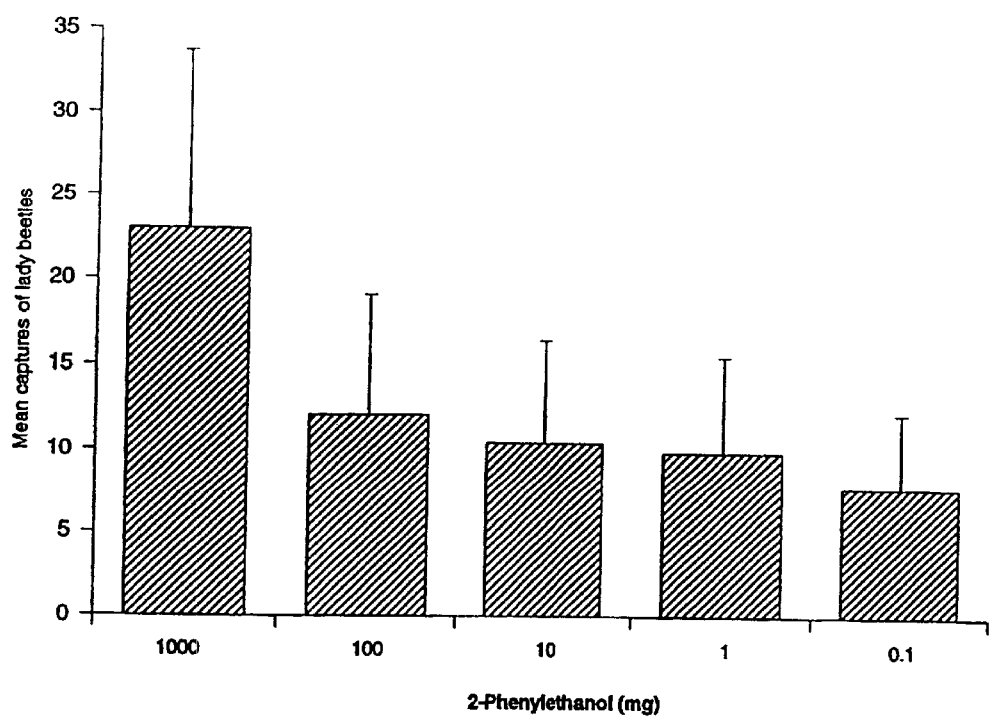
FIG. 12. Shows the relationship between dose of 2-phenyl ethanol on a cotton wick and the capture of *Coleomegilla maculata* adults in an alfalfa field. Bars above the means indicate standard errors, and means having no letters in common are significantly different from each other (ANOVA, FPLSD test, P<0.05).
Figure 13:
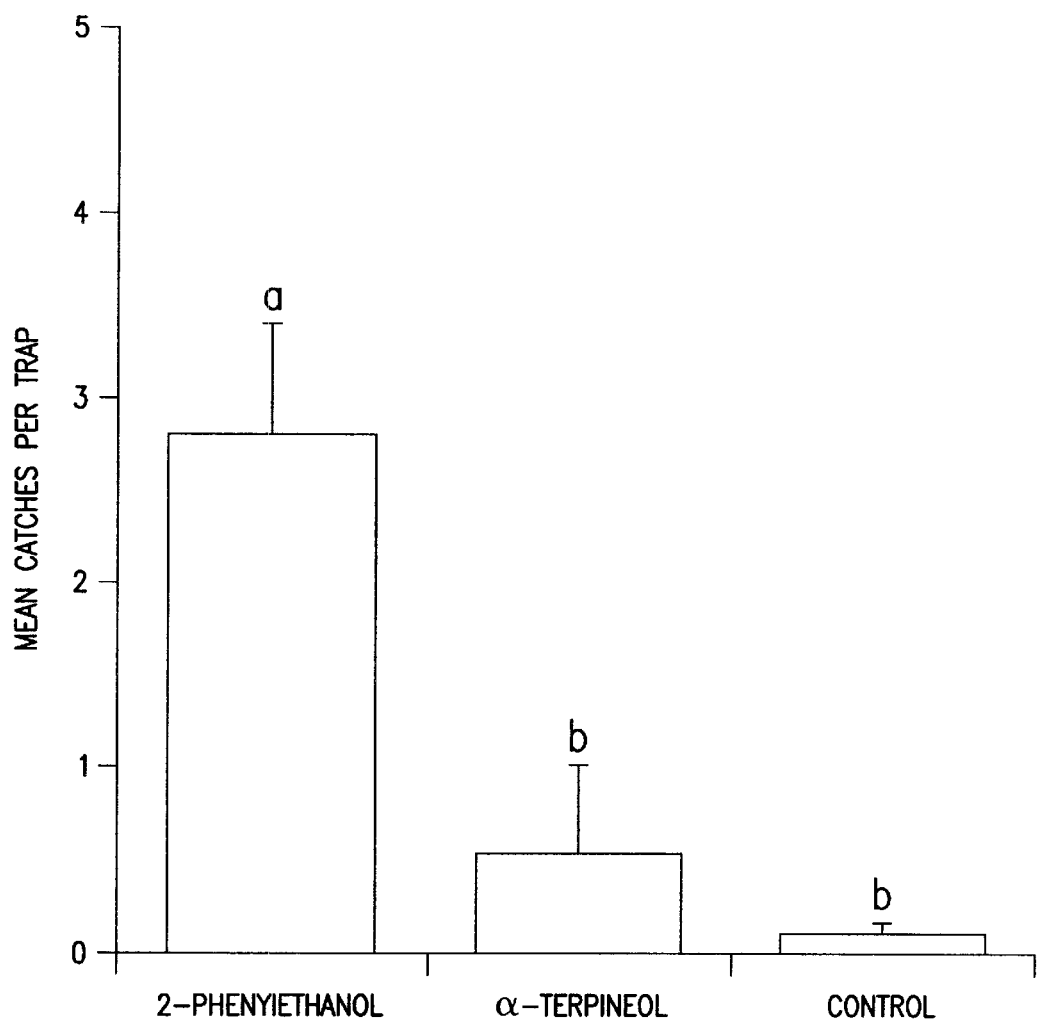
FIG. 13. Shows the mean number of *Chrysoperla carnea* adults captured per night in Wisconsin cranberry marshes. Bars above the means indicate standard errors, and means having no letters in common are significantly different from each other (ANOVA, FPLSD test, P<0.05).

The results from field trapping test showed that both *C. maculata* and *C. carnea* were significantly attracted to 2-phenylethanol (FIG. 6). Significant catches of *C. maculata* were also observed from traps baited with α-terpineol.

Discussion

This is the first report of successful EAG recordings from the two predatory insect species, *C. maculata* and *C. carnea*. The positive EAG responses to semiochemicals released from their prey species and their host plants indicate that these two predators use such chemicals to locate their prey. These EAG-active compounds, have behavioral activities as attractants or arrestants, can be used to enhance the efficacy of these two predaceous insects in pest management systems. Emitting these compounds in a cropping system attracts lady beetles and lacewings to their target habitats, and retains them in habitats for longer durations.

Volatiles from corn plants contain general and specific odor components including aliphatic and aromatic alcohols, aldehydes, and derivative esters, as well a variety of monoterpenes and sesquiterpenes and their associated alcohols, aldehydes, and derivative esters (Hammack, L., 1997, Environmental Entomology Vol. 26, No. 2. p311–317; Flath, R. A., et al., 1978, Journal of Agricultural Food and chemistry Vol, 26, No. 6, 1290–1293; and Hibbard, B. E., et al., 1997, *Enviornmental Entomology,* 26, 285–295). Many parasitoids and predators use semiochemicals associated with the host or the host habitat to locate their prey (Udayagiri, S., 1996, *Agric. Zool. Rev.* 7:181–216; Turlings, T. C. J., et al., 1992, Learning of host-finding cues by hymenopterous parasitoids, pp. 51–78, in A. C. Lewis and D. R. Papaj (eds.). Insect Learning: Ecological and Evolutionary Perspectives. Chapman and Hall, New York.). In coccinellids, Obata, S., 1986, *Entomophaga.* 31:303–311 reported that chemical cues could be involved in prey finding.

EAG responses from the antennae of *C. maculata* elicited by corn volatile components including (E)-β-farnesene, α-terpineol, 2-phenylethanol, β-caryophyllene, (Z)-3-hexanol, hexanol and 1-octen-3-ol demonstrate that this predator responds to odors from host habitats for prey location. Field trapping results showed that adult *C. maculata* were attracted to at least two components, a-terpineol and 2-phenylethanol.

Among the seven corn volatile compounds found to be EAG-active in *C. maculata*, (E)-β-farnesene has also been reported as an aphid alarm pheromone component (Nault, L. R., et al., 1973, *Environmental Entomology,* 2 101–105). This compound is emitted from aphids when they are disturbed. The perception of this pheromone by aphids leads to dispersal from their feeding sites. Behavioral test results showed that two lady beetle species, *Hippodamia convergens* and *Harmonia axyridis* were attracted by this compound. This compound, however, does not elicit searching behaviors in another lady beetle, *Coccinella septempunctata* (Nakamuta, K., 1991, *Appl. Ent. Zool.* 26:1–7). The active EAG response recorded from the antennae of *C. maculata* to this compound could also be a result of responding to corn volatiles, as (E)-β-farnesene is also a common compound among corn leaf volatiles, though it is generally found together with other sesquiterpene hydrocarbons. Colburn, R., and Asquith, D., 1970, *J. Econ. Entomol.* 63:1376–1377, have shown that odors from mite infested plants, including (E)-β-farnesene, are used by adults of the ladybird beetle, *Stethorus punctum* to select host plants. However, no differences in catches were found from the traps baited with this compound compared to those of the control.

Chemicals secreted by aphids other than (E)-β-farnesene, for example breakdown products of honeydew, are known to cue local search by lady beetles (Evans, E. W., and Richards, D. R., 1997, *Entomophaga* 42:93–102). Sex pheromone communication in mate finding was demonstrated in aphids in the genus Schizaphis (Pettersson, J., 1971, *Entomol. Scand.* 1:63–73). Virgin females (oviparae) release a male-attracting pheromone from scent plaques on their metathoracic tibiae. Dawson, G. W., et al., 1989, *Pure Appl. Chem.* 61:555–558 identified sex pheromones of several aphid species as a combination of (4aS,7S,7aR)-nepetalactone and (1R,4aS,7S,7aR)-nepetalactol.

The present study shows that antennae of adult *C. maculata* responded with significant EAGs to these two components of aphid sex pheromone, which indicates that *C. maculata* may use them or similar compounds in prey finding. Significant EAG responses were also observed from the antennae of *C. maculata* in response to the extract of catnip, which is explained because (4aS,7S,7aR)-nepetalactone is a major constituent in essential oil of *N. cataria* (Eisenbraun, E. J., et al., 1980, *J. Org. Chem.* 45:3811–3814).

As adult *C. carnea* are reported most active at twilight or during the night (Duelli, P. 1984. Flight, dispersal, migration. In Biology of Chrysopidae. (Canard M., Semeria Y., and New T. R., eds). W. Junk, The Hague, pp. 129–133) when the use of visual cues are impaired, positive EAG responses to plant volatile compounds and sex pheromones of their prey species indicate that chemical orientation is involved in prey host location. Van Emden and Hagen (1976) found that tethered *C. carnea* females responded positively in flight toward isomers of tryptophan and their breakdown products. Our results show that the antennae of *C. carnea* are highly sensitive to two corn leaf volatiles, (E)-β-farnesene and 2-phenylethanol. However, in the field trapping study test *C. carnea* were only found to be attractive to the latter compound. The recorded EAG response to (E)-β-farnesene from *C. carnea* is different from the results obtained from the Asian lacewing species, *Chrysopa cognata* (Boo, K. S., et al., 1998, J. Chem. Ecol. (in press)). Significant EAG responses elicited by 2-phenylethanol at a relative lower dose indicate the ability of *C. carnea* to detect the compound at a greater distance from its source.

An earlier study showed that β-caryophyllene acts as an attractant to adults of *C. carnea* in the field (Flint, H. M., et al., 1979, *Environ. Entomol.* 8:1123–1125). However, our present EAG study showed a relatively low EAG response obtained from the antennae of *C. carnea*, and low catches of *C. carnea* in a field test. The significant EAG responses from *C. carnea* to sex pheromones of their prey aphid species presented here suggest that both males and females locate their prey by responding to these compounds. Boo et al. (1998) reported that adult *C. cognata* are attracted to (4aS, 7S,7aR)-nepetalactone and mixtures of this compound with (1R,4aS,7S,7aR)-nepetalactol in the field.

The present EAG experiments, demonstrate that the female extracts of *C. maculata* elicited significant EAG responses from male conspecific antennae, which suggest that the substances from females could be used as sex pheromone for mate finding.

Summary

Electroantennograms (EAGs) were recorded from two predatory insect species, the twelve spotted lady beetle, *Coleomegilla maculata* (Coleoptera: Coccinellidae) and the green lacewing, *Chrysoperla carnea* (Neuroptera: Chrysopidae) in response to semiochemicals emitted from one of their prey species, the pea aphid, *Acyrthosiphon pisum*, (Homoptera: Aphididae) and their host plant. EAG responses were also recorded from *C. maculata* in response to extracts from individuals of the opposite sex, and extracts from an herbaceous plant, catnip, *Nepeta cataria*.

Extracts of catnip and two sex pheromone components of aphids, (4aS,7S,7aR)-nepetalactone and (1R,4aS,7S,7aR)-nepetalactol, elicited significant EAG responses from the antennae of both predatory species. Of ten corn volatile compounds tested, *C. carnea* adults responded most strongly to 2-phenylethanol and (E)-β-farnesene. A significant difference in EAG response to extracts of corn leaf collections was observed between male and female *C. carnea*. In *C. maculata*, significant EAG responses were elicited by most of the tested corn volatile compounds, except α-pinene and (E)-2-hexanal. The highest EAG responses were observed in response to (E)-β-farnesene, α-terpineol, 2-phenylethanol and β-caryophyllene.

Sexual differences in EAG responses of *C. maculata* were only found in response to 1-octen-3-ol. Male antennae of *C. maculata* produced significant EAG responses to extracts from conspecific females, but not to males, which indicates that chemicals from females are involved in sexual communication. A significant EAG response was also recorded in response to the extracts of fluids produced during "reflex bleeding". Male and female antennae of both species exhibited similar dose response curves to most of the selected compounds, although female *C. maculata* antennae exhibited higher thresholds in response to several compounds including a-terpineol, (Z)-3-hexenol and (4aS,7S,7aR)-nepetalactone, respectively. Field tests showed that 2-phenylethanol was highly attractive to adults of both species, while *C. maculata* was attracted to traps baited with a-terpineol.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for attracting a predatory insect selected from the family group consisting of Coccinellidae and Chrysopidae to a target area, comprising applying an effective attracting amount of a plant volatile selected from the group consisting of α-terpineol, phenyl alcohol, phenyl ester, phenyl aldehyde, and phenyl ketone.

2. The method of claim 1 wherein the predatory insect is of the species *Colemegilla maculata*.

3. The method of claim 1 wherein the predatory insect is of the species *Chrysoperla carnea*.

4. The method of claim 1 wherein the plant volatile is 2-phenylethanol.

5. The method of claim 1 wherein the plant volatile is phenylacetaldehyde.

6. The method of claim 1 wherein the target area is a farm field, a garden, or a horticultural or floricultural nursery.

7. The method of claim 1 wherein the plant volatile is applied by broadcast or restricted localized spraying.

8. The method of claim 1 wherein the plant volatile is applied by placing one or more controlled-release point-source dispensers in or around the target area.

* * * * *